(12) United States Patent
Kelly

(10) Patent No.: US 7,511,187 B2
(45) Date of Patent: Mar. 31, 2009

(54) ABSORBENT ARTICLE HAVING STAIN MASKING CHARACTERISTICS

(75) Inventor: William G. F. Kelly, Middlesex, NJ (US)

(73) Assignee: McNeil - PPC Inc., Skillman, NJ (US)

( * ) Notice: Subject to any disclaimer, the term of this patent is extended or adjusted under 35 U.S.C. 154(b) by 265 days.

(21) Appl. No.: 10/800,093

(22) Filed: Mar. 12, 2004

(65) Prior Publication Data
US 2005/0203471 A1 Sep. 15, 2005

(51) Int. Cl.
*A61F 13/15* (2006.01)
*A61F 13/20* (2006.01)

(52) U.S. Cl. ........................... 604/368; 604/367

(58) Field of Classification Search ................ 604/367, 604/368
See application file for complete search history.

(56) References Cited

U.S. PATENT DOCUMENTS

| | | | |
|---|---|---|---|
| 3,684,649 A * | 8/1972 | Shelton et al. | 428/514 |
| 4,868,031 A | 9/1989 | Modrak et al. | |
| 5,667,619 A | 9/1997 | Alikhan et al. | |
| 6,180,052 B1 | 1/2001 | Ouellette et al. | |
| 6,395,956 B1 * | 5/2002 | Glasgow et al. | 604/378 |
| 2002/0193492 A1 * | 12/2002 | Wilson | 524/437 |
| 2004/0253894 A1 * | 12/2004 | Fell et al. | 442/381 |

FOREIGN PATENT DOCUMENTS

| | | | |
|---|---|---|---|
| EP | 0951889 A | | 10/1999 |
| EP | 951889 A1 * | | 10/1999 |
| EP | 1344512 A | | 9/2003 |
| EP | 1 430 861 A | | 6/2004 |
| EP | 1 510 192 A | | 3/2005 |
| EP | 1 574 192 A | | 9/2005 |
| EP | 1 574 324 A | | 9/2005 |
| WO | WO 93/12749 A | | 7/1993 |
| WO | WO 9312749 A1 * | | 7/1993 |
| WO | WO 9428846 A | | 12/1994 |

OTHER PUBLICATIONS

European Search Report EP 05 25 1481 dated Jul. 11, 2005.
International Search Report PCT/US2005/025561 dated Mar. 17, 2006.

* cited by examiner

*Primary Examiner*—Tatyana Zalukaeva
*Assistant Examiner*—Melanie J Hand

(57) ABSTRACT

A sanitary napkin including a body-facing cover layer and an absorbent system adjacent the cover layer for receiving liquid therefrom, the napkin having a masking value of less than about 115,000, an average fluid penetration time of less than about 45 seconds and an average rewet of less than about 0.05 grams according to the test procedure described herein.

24 Claims, 17 Drawing Sheets

21

141a

ABSORBENT ARTICLE HAVING STAIN MASKING CHARACTERISTICS

FIELD OF THE INVENTION

The present invention generally relates to an absorbent article such as a feminine sanitary napkin. More particularly, the present invention relates to a sanitary napkin having improved fluid-handling and stain masking properties.

BACKGROUND OF THE INVENTION

The use of apertured films in personal care products, such as feminine sanitary napkins, is well known in the art. These films may be used as body-contacting facing layers, as fluid handling layers or as other components of personal care products. When such films are used in feminine sanitary protection articles as the body-contacting facing layer, it has been generally found that the higher the open area of the film, the more effectively the film will transfer menstrual fluid to underlying layers (e.g., transfer layer, absorbent core) of the article. Unfortunately, it has also be found that the higher the open area of the film, the less effective the film is at stain "masking" the absorbed menstrual fluid once the menstrual fluid has been transferred to the underlying layers of the article. That is, the higher the open area of the film, the more visible the menstrual fluid stain will be after it is absorbed by the article.

It is object of the present invention to provided an absorbent article having improved fluid-handling properties. More particularly, it is an object of the present invention to provide an absorbent article having improved fluid handling properties while at the same time having effective stain masking characteristics.

SUMMARY OF THE INVENTION

In view of the foregoing, the present invention provides a sanitary napkin including a body-facing cover layer and an absorbent system adjacent said cover layer for receiving liquid therefrom, the napkin having a masking value of less than about 1115,000, an average fluid penetration time of less than about 45 seconds and an average rewet of less than about 0.05 grams according to the test procedure described herein.

BRIEF DESCRIPTION OF THE FIGURES

FIG. 1b is a sectional view taken along line B as indicated in FIG. 1a;

DETAILED DESCRIPTION OF THE OF THE INVENTION

The present invention is directed to an absorbent article, such as a feminine sanitary napkin, that has improved fluid handling capabilities while at the same time exhibits effective stain masking characteristics.

Figure 12:
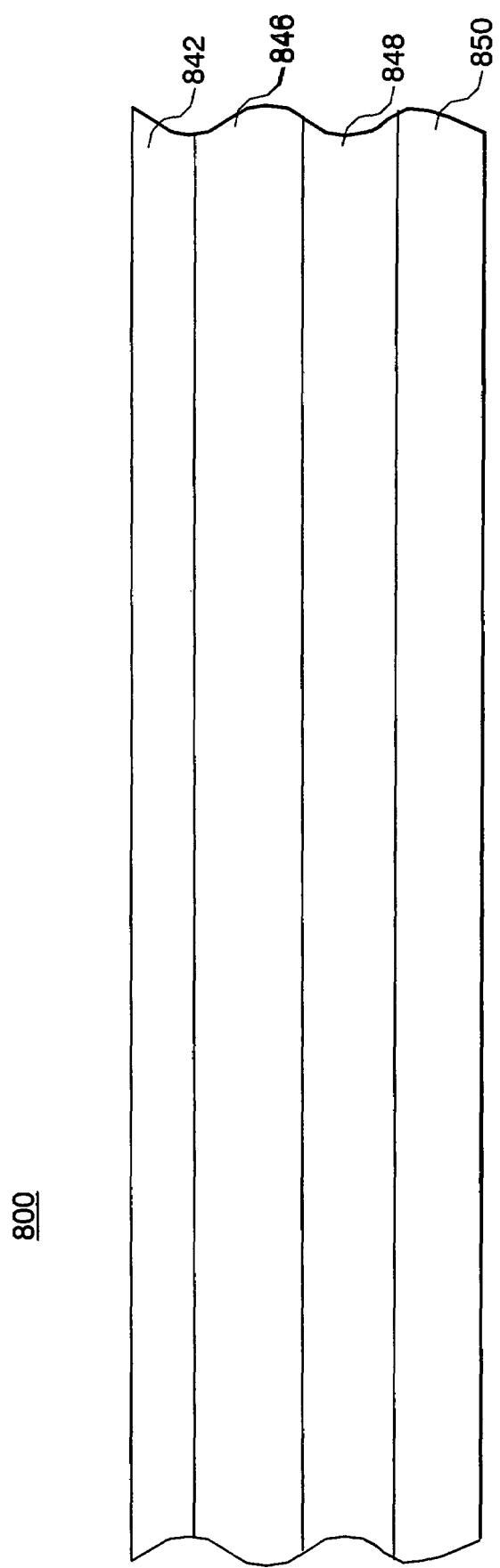
FIG. 12 is cross sectional view of an absorbent article according to a first embodiment of the present invention.

Referring to FIG. 12, there is shown a first embodiment of the present invention, a sanitary napkin 800. The sanitary napkin 800 includes a cover layer 842, a first absorbent layer 846, a second absorbent layer 848 and a barrier layer 850. Each of these layers are described in further detail below.

Cover Layer

The cover layer 842 is preferably an apertured film material and more preferably the cover layer 842 is an apertured film material of the type described in greater detail below with reference to FIGS. 1-9 and 11.

Reference is now made to FIGS. 1a-1e which depict an apertured film 10 which may be used as the cover layer 842 of the absorbent article according to the present invention. The film 10 includes a plurality of repeating interconnected frames 12. In the embodiment shown in FIGS. 1a-1e, each frame 12 includes opposed end regions 12a and 12b and opposed side walls 12c and 12d. Each of the end regions 12a and 12b being in spaced relationship to one another and each of the opposed side walls 12c and 12d being in spaced relationship to one another. In the specific embodiment shown in FIGS. 1a-1d, each of the frames 12 are interconnected to an adjacent frame 12. More particularly, as shown, each frame 12 "shares" a common side wall 12c, 12d, with a directly adjacent frame 12. Likewise, each frame 12 shares a common end region 12a, 12b with a directly adjacent frame 12. The apertured film 10 further includes first and second cross members 14a and 14b. As shown, cross member 14b extends from a first side wall 12c to an opposed side wall 12d of the frame 12. Likewise, cross member 14a extends from a end region 12a to the opposed end region 12b. In the embodiment of the invention shown in FIGS. 1a-1e, the cross members 14a and 14b intersect at the center of the frame is shown. In addition, in the embodiment of the invention shown in FIGS. 1a-1e, the cross members 14a and 14b are arranged such that they are orthogonally arranged to one another.

Figure 1A:
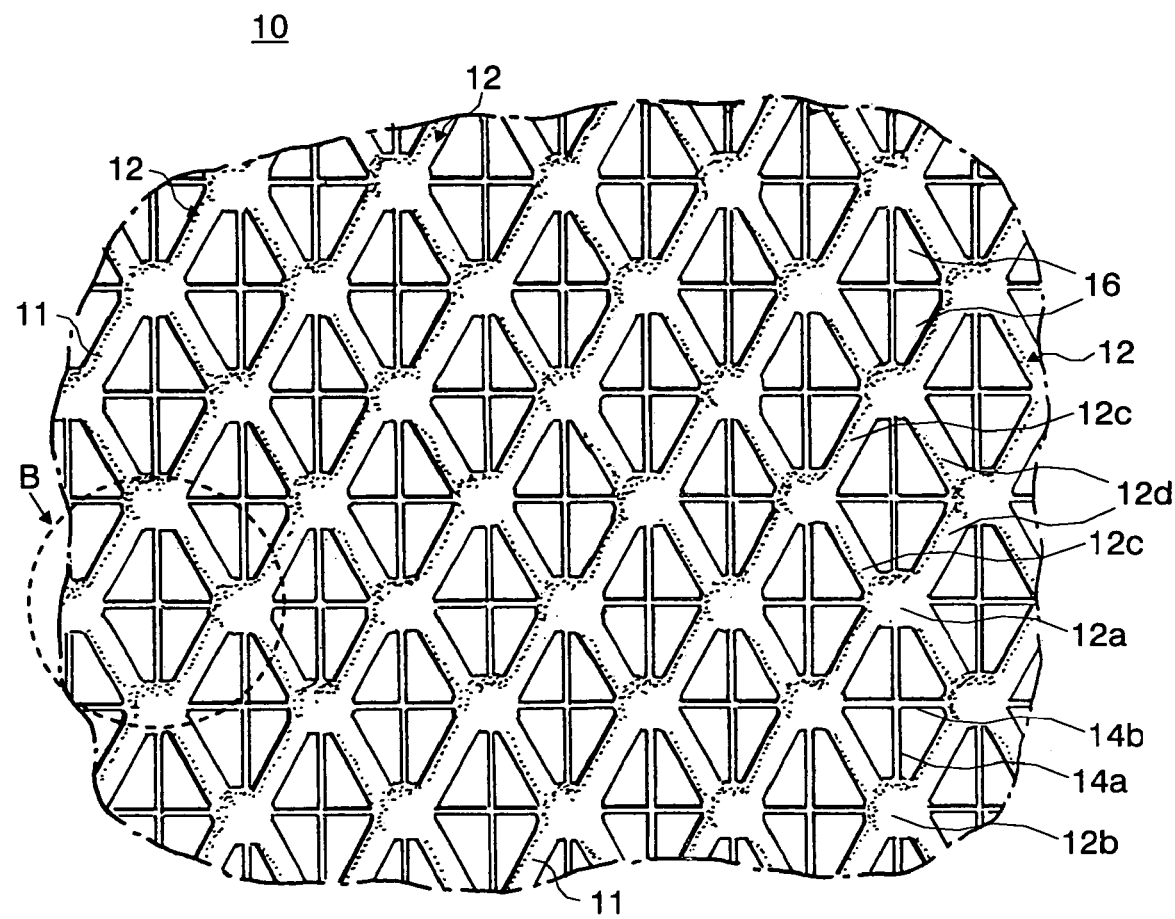
FIG. 1a is a schematic view of a three-dimensional film for use as a cover layer in the absorbent article according to the present invention.

Although the embodiment of the invention shown in FIGS. 1a-1d shows the apertured film as having two cross members 14a and 14b, it is possible that only a single cross member could be employed as long as the cross member extends substantially across an open area defined by the frame 12. Also, although the frame 12 has been shown as being generally hexagonal in shape, it is possible that other shapes be used for the frame 12. The cross members 14a and 14b preferably have a width in the range of about 0.008 mils to about 0.024 mils. The film 10 may optionally include a plurality of bumps 11 or the like arranged on the surface of the film as best seen in FIG. 1a.

Figure 1B:
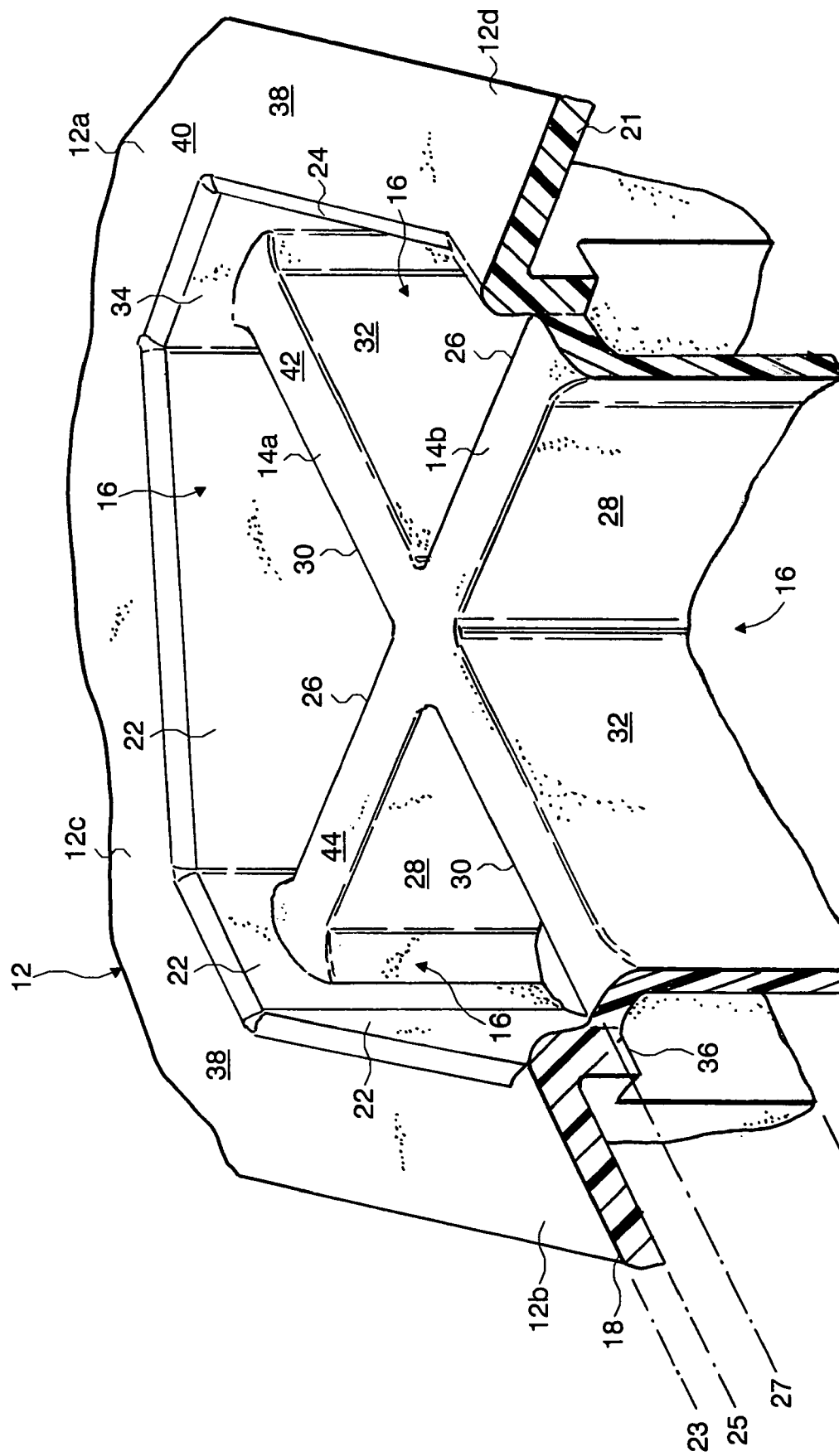

The film 10 further includes a plurality of apertures 16. Each aperture 16 is bound by at least a portion of the frame 12 and at least a portion of one of the cross members 14a and 14b. Reference is now made to FIG. 1b which is an illustration of a cross-section of the film 10 shown in FIG. 1 taken along line A of FIG. 1a. Each aperture is bound by at least a portion of each of the cross members 14a and 14b as well as by a portion of the frame 12. More particularly, as best seen in FIG. 1b, each of the apertures 16 is bound by a corresponding interior wall 22, 24 of a respective side wall 12c, 12d of the frame portion 12. Each aperture 16 is further bound by a corresponding interior wall 26 or 28 of cross member 14b and a corresponding interior wall 30, 32 of cross member 14a. Finally, each aperture 16 is bound by a respective interior wall 34, 36 of a corresponding end region 12a, 12b.

Again referring to FIG. 1b, film 10 generally includes a first generally planar top surface 18 in imaginary plane 23 and an opposed, generally planar, second bottom surface 21 in imaginary plane 25. The top surface 38 of the side walls 12c and 12d and the top surface 40 of the end regions 12a and 12b are coplanar with plane 23. However, the top surfaces 42 and 44 of cross members 14a and 14b are recessed relative to plane 23. More particularly, the top surfaces 42 and 44 of cross members 14a and 14b are located in a plane 27 located below both planes 23 and 25. Preferably the top surfaces 42 and 44 of the cross members 14a and 14b are recessed relative to the top surface 18 of the film, i.e., recessed relative to plane 23, to a depth in the range of about 5.0 mils to about 17.0 mils. The top surfaces 42 and 44 of cross members 14a and 14b are preferably substantially parallel to the imaginary planes 23 and 25.

Figure 1C:
FIG. 1c is an enlarged photomicrograph of the three-dimensional film schematically shown in FIG. 1a, showing a top surface thereof.
Figure 1D:
FIG. 1d is an enlarged photomicrograph of the three-dimensional film schematically shown in FIG. 1b, showing a bottom surface thereof.

As best seen in FIGS. 1c and 1d, interior walls 22, 24 of side walls 12c and 12d, interior walls 26, 28 of cross member 14a, interior walls 30, 32 of cross member 14b, and interior walls 34, 36 of end regions 12a, 12b cooperate to define the apertures 16 and each of these interior walls extend below plane 25 such that the bottom opening of each aperture 16 is located below the bottom planar surface 21 of the film, i.e., below imaginary plane 25. More specifically, interior walls 22, 24 of side walls 12c and 12d, interior walls 26, 28 of cross member 14a, interior walls 30, 32 of cross member 14b, and interior walls 34, 36 of end regions 12a, 12b extend downwardly such that the bottom opening of each aperture is located in imaginary plane 29 which is located below imaginary planes 23, 25 and 27. It is noted that imaginary planes 23, 25, 27 and 29 are all substantially parallel to one another.

Since the top surfaces 42, 44 of the cross members 14a and 14b are recessed relative to the top surface 18 of the film 10, i.e., recessed relative to imaginary plane 23, a first relatively large aperture is effectively defined from the top surface 18 of the film 10 to the top surfaces 42, 44 of the cross members. The cross members 14a and 14b act to divide this larger aperture in to four relatively smaller apertures which are in communication with the larger aperture from the top surfaces 42, 44 of the cross members 14a and 14b through the bottom opening of each aperture 16. Stated another way, within each frame member 12, a relatively large aperture is defined from plane 23 to plane 27 and a plurality of relatively smaller apertures, that are communication with the larger aperture, are defined from plane 27 to plane 29. In the embodiment shown in FIGS. 1a-1d, each of the smaller apertures defined from plane 27 to plane 29 have an area that is less than one quarter of the total area of the larger aperture defined from plane 23 to 27. In an embodiment in which a single cross member was employed, each of the smaller apertures defined by the cross member would have an area less than one half the total area of the larger aperture. The reader is advised that for simplicity and clarity in the drawings, both the "smaller" and "larger" apertures discussed above are generally identified by reference numeral 16 herein.

The apertured films according to the present invention preferably have an open area in the range about 20% to about 30%. Open area may be determined by using image analysis to measure the relative percentages of apertured and unapertured, or land, areas. Essentially image analysis converts an optical image from a light microscope into an electronic signal suitable for processing. An electronic beam scans the image, line-by-line. As each line is scanned, an output signal changes according to illumination. White areas produce a relatively high voltage and black areas a relatively low voltage. An image of the apertured formed film is produced and, in that image, the holes are white, while the solid areas of thermoplastic material are at various levels of gray.

The more dense the solid area, the darker the gray area produced. Each line of the image that is measured is divided into sampling points or pixels. The following equipment can be used to carry out the analysis described above: a Quantimet Q520 Image Analyzer (with v. 5.02B software and Grey Store Option), sold by LEICA/Cambridge Instruments Ltd., in conjunction with an Olympus SZH Microscope with a transmitted light base, a plan 1.0.times. objective, and a 2.50.times. eyepiece. The image can be produced with a DAGE MTI CCD72 video camera.

A representative piece of each material to be analyzed is placed on the microscope stage and sharply imaged on the video screen at a microscope zoom setting of 10.times. The open area is determined from field measurements of representative areas. The Quantimet program output reports mean value and standard deviation for each sample.

A suitable starting film for making a three-dimensional apertured film according to the present invention is a thin, continuous, uninterrupted film of thermoplastic polymeric material. This film may be vapor permeable or vapor impermeable; it may be embossed or unembossed; it may be corona-discharge treated on one or both of its major surfaces or it may be free of such corona-discharge treatment; it may be treated with a surface active agent after the film is formed by coating, spraying, or printing the surface active agent onto the film, or the surface active agent may be incorporated as a blend into the thermoplastic polymeric material before the film is formed. The film may comprise any thermoplastic polymeric material including, but not limited to, polyolefins, such as high density polyethylene, linear low density polyethylene, low density polyethylene, polypropylene; copolymers of olefins and vinyl monomers, such as copolymers of ethylene and vinyl acetate or vinyl chloride; polyamides; polyesters; polyvinyl alcohol and copolymers of olefins and acrylate monomers such as copolymers of ethylene and ethyl acrylate and ethylenemethacrylate. Films comprising mixtures of two or more of such polymeric materials may also be used. The machine direction (MD) and cross direction (CD) elongation of the starting film to be apertured should be at least 100% as determined according to ASTM Test No. D-882 as performed on an Instron test apparatus with a jaw speed of 50 inches/minute (127 cm/minute). The thickness of the starting film is preferably uniform and may range from about 0.5 to about 5 mils or about 0.0005 inch (0.0013 cm) to about 0.005 inch (0.076 cm). Coextruded films can be used, as can films that have been modified, e.g., by treatment with a surface active agent. The starting film can be made by any known technique, such as casting, extrusion, or blowing.

A method of aperturing the film involves placing the film onto the surface of a patterned support member. The film is subjected to a high fluid pressure differential as it is on the support member. The pressure differential of the fluid, which may be liquid or gaseous, causes the film to assume the surface pattern of the patterned support member. If the patterned support member has apertures therein, portions of the film overlying the apertures may be ruptured by the fluid pressure differential to create an apertured film. A method of forming an apertured film is described in detail in commonly owned U.S. Pat. No. 5,827,597 to James et al., incorporated herein by reference.

Such a three dimensional apertured film is preferably formed by placing a thermoplastic film across the surface of an apertured support member with a pattern corresponding to desired final film shape. A stream of hot air is directed against the film to raise its temperature to cause it to be softened. A vacuum is then applied to the film to cause it to conform to the shape of the surface of the support member. Portions of the film lying over the apertures in the support member are further elongated until rupture to create apertures in the film.

Figure 2:
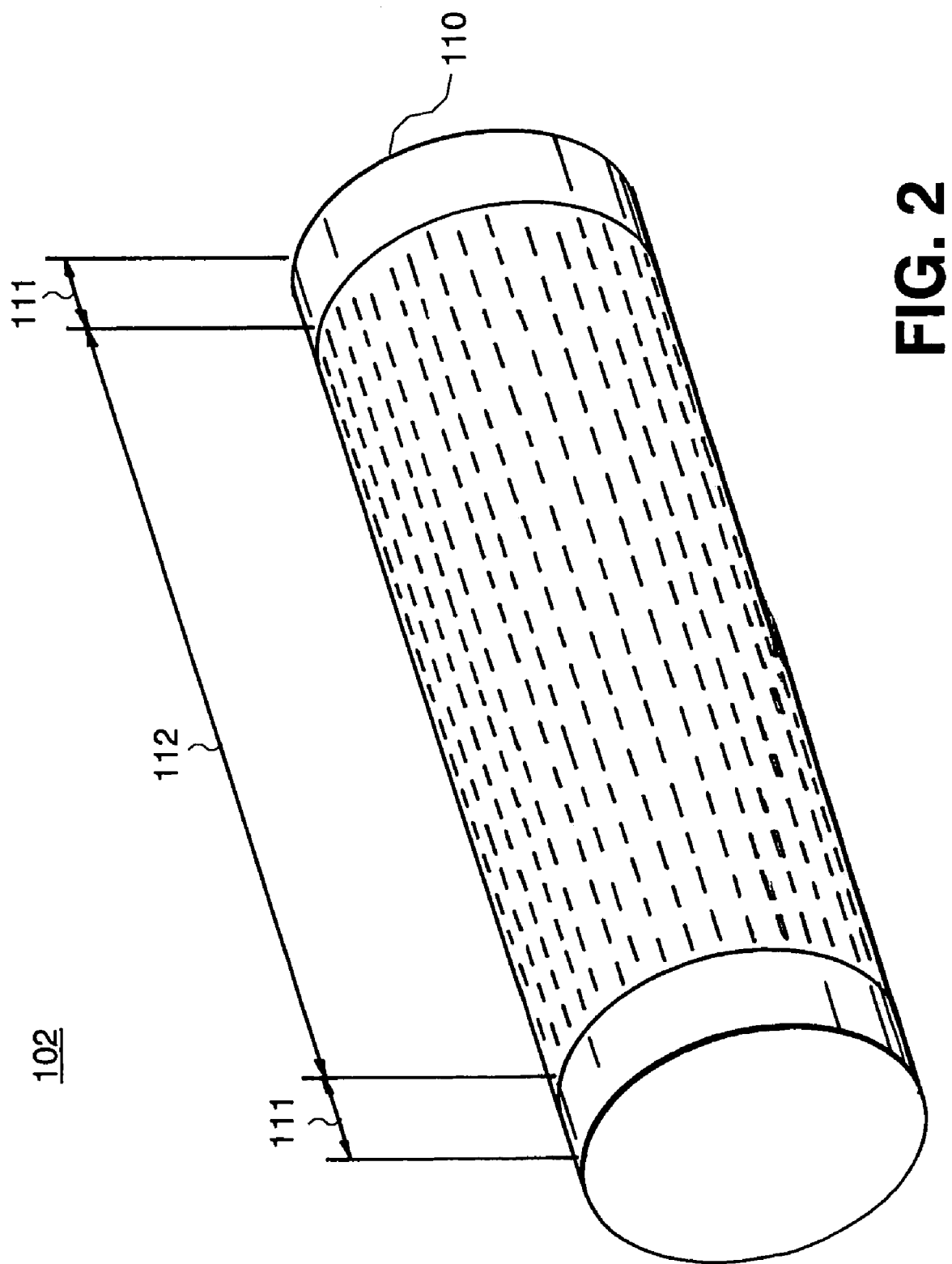
FIG. 2 is a schematic illustration of one type of three dimensional topographical support member useful to make a film of the present invention.

A suitable apertured support member for making these three-dimensional apertured films is a three-dimensional topographical support member made by laser sculpting a workpiece. A schematic illustration of an exemplary workpiece that has been laser sculpted into a three dimensional topographical support member is shown in FIG. 2.

The workpiece 102 comprises a thin tubular cylinder 110. The workpiece 102 has non-processed surface areas 111 and a laser sculpted center portion 112. A preferred workpiece for producing the support member of this invention is a thin-walled seamless tube of acetal, which has been relieved of all residual internal stresses. The workpiece has a wall thickness of from 1-8 mm, more preferably from 2.5-6.5 mm. Exemplary workpieces for use in forming support members are one to six feet in diameter and have a length ranging from two to sixteen feet. However, these sizes are a matter of design choice. Other shapes and material compositions may be used for the workpiece, such as acrylics, urethanes, polyesters, high molecular weight polyethylene and other polymers that can be processed by a laser beam.

Figure 3:
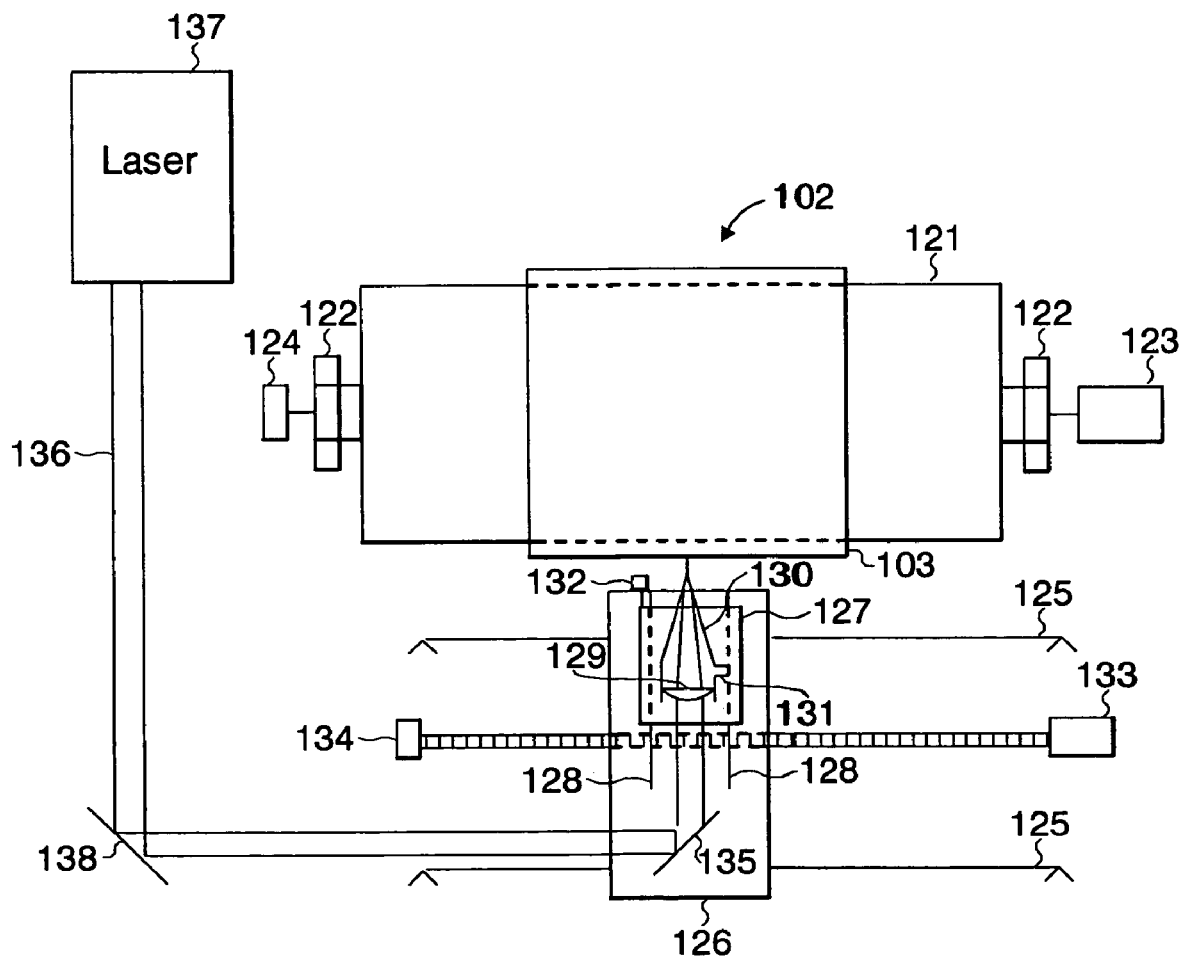
FIG. 3. is a schematic illustration of an apparatus for laser sculpting a workpiece to form a three dimensional topographical support member useful to make a film of the present invention.

Referring now to FIG. 3, a schematic illustration of an apparatus for laser sculpting the support member is shown. A starting blank tubular workpiece 102 is mounted on an appropriate arbor or mandrel 121 that fixes it in a cylindrical shape and allows rotation about its longitudinal axis in bearings 122. A rotational drive 123 is provided to rotate mandrel 121 at a controlled rate. Rotational pulse generator 124 is connected to and monitors rotation of mandrel 121 so that its precise radial position is known at all times.

Parallel to and mounted outside the swing of mandrel 121 is one or more guide ways 125 that allow carriage 126 to traverse the entire length of mandrel 121 while maintaining a constant clearance to the top surface 103 of workpiece 102. Carriage drive 133 moves the carriage along guide ways 125, while carriage pulse generator 134 notes the lateral position of the carriage with respect to workpiece 102. Mounted on the carriage is focusing stage 127. Focusing stage 127 is mounted in focus guide ways 128. Focusing stage 127 allows motion orthogonal to that of carriage 126 and provides a means of focusing lens 129 relative to top surface 103. Focus drive 132 is provided to position the focusing stage 127 and provide the focusing of lens 129.

Secured to focusing stage 127 is the lens 129, which is secured in nozzle 130. Nozzle 130 has means 131 for introducing a pressurized gas into nozzle 130 for cooling and maintaining cleanliness of lens 129. A preferred nozzle 130 for this purpose is described in U.S. Pat. No. 5,756,962 to James et al. which is incorporated herein by reference.

Also mounted on the carriage 126 is final bending mirror 135, which directs the laser beam 136 to the focusing lens 129. Remotely located is the laser 137 with optional beam bending mirror 138 to direct the beam to final beam bending mirror 135. While it would be possible to mount the laser 137 directly on carriage 126 and eliminate the beam bending mirrors, space limitations and utility connections to the laser make remote mounting far preferable.

When the laser 137 is powered, the beam 136 emitted is reflected by first beam bending mirror 138, then by final beam bending mirror 135, which directs it to lens 129. The path of laser beam 136 is configured such that, if lens 129 were removed, the beam would pass through the longitudinal center line of mandrel 121. With lens 129 in position, the beam may be focused above, below, at, or near top surface 103.

While this apparatus could be used with a variety of lasers, the preferred laser is a fast flow $CO_2$ laser, capable of producing a beam rated at up to 2500 watts. However, slow flow $CO_2$ lasers rated at 50 watts could also be used.

Figure 4:
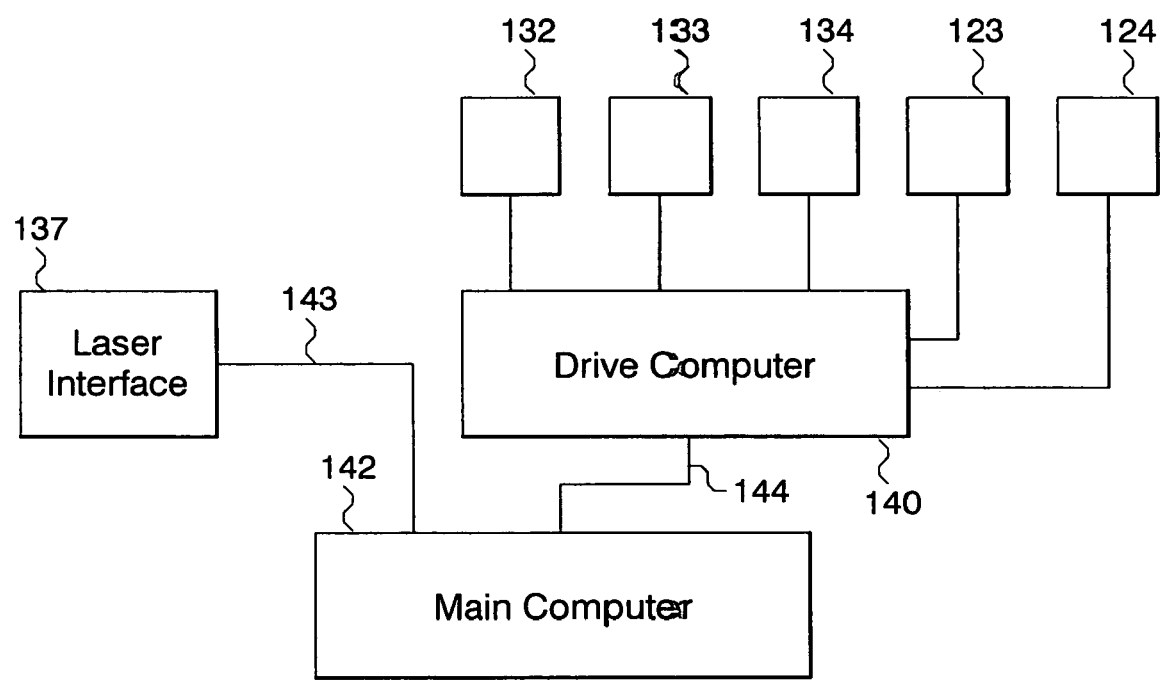
FIG. 4 is a schematic illustration of a computer control system for the apparatus of FIG. 3.

FIG. 4 is a schematic illustration of the control system of the laser sculpting apparatus of FIG. 3. During operation of the laser sculpting apparatus, control variables for focal position, rotational speed, and traverse speed are sent from a main computer 142 through connection 144 to a drive computer 140. The drive computer 140 controls focus position through focusing stage drive 132. Drive computer 140 controls the rotational speed of the workpiece 102 through rotational drive 123 and rotational pulse generator 124. Drive computer 140 controls the traverse speed of the carriage 126 through carriage drive 133 and carriage pulse generator 134. Drive computer 140 also reports drive status and possible errors to the main computer 142. This system provides positive position control and in effect divides the surface of the workpiece 102 into small areas called pixels, where each pixel consists of a fixed number of pulses of the rotational drive and a fixed number of pulses of the traverse drive. The main computer 142 also controls laser 137 through connection 143.

A laser sculpted three dimensional topographical support member may be made by several methods. One method of producing such a support member is by a combination of laser drilling and laser milling of the surface of a workpiece.

Methods of laser drilling a workpiece include percussion drilling, fire-on-the-fly drilling and raster scan drilling.

Figure 11:
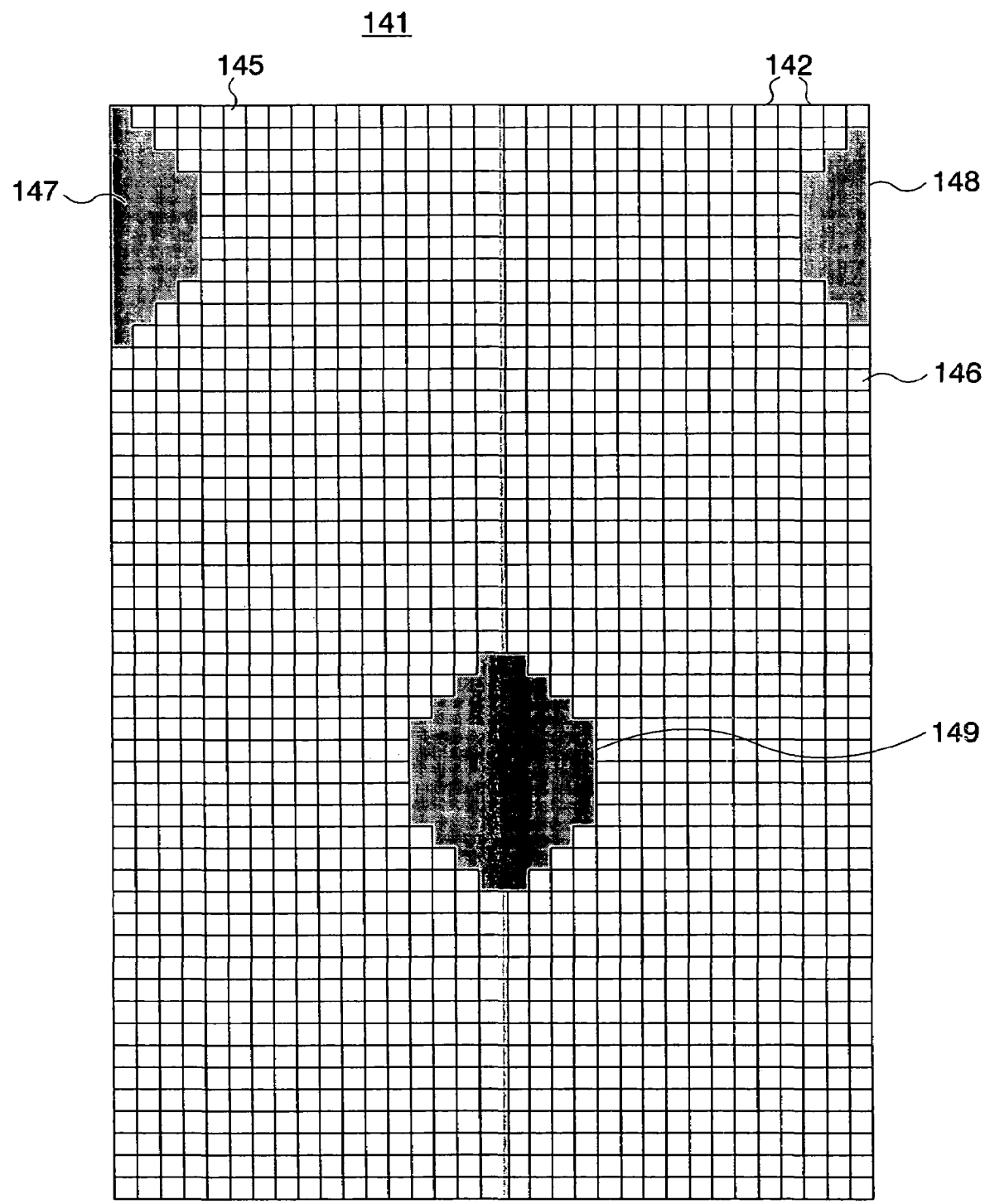
FIG. 11 is a graphical representation of a file to laser sculpt a workpiece to produce a three dimensional topographical support member for producing an apertured film.

A preferred method is raster scan drilling. In this approach, the pattern is reduced to a rectangular repeat element 141 as depicted in FIG. 11. This repeat element contains all of the information required to produce the desired pattern. When used like a tile and placed both end-to-end and side-by-side, the larger desired pattern is the result.

The repeat element 141 is further divided into a grid of smaller rectangular units or "pixels" 142. Though typically square, for some purposes, it may be more convenient to employ pixels of unequal proportions. The pixels themselves are dimensionless and the actual dimensions of the image are set during processing, that is, the width 145 of a pixel and the length 146 of a pixel are only set during the actual drilling operation. During drilling, the length of a pixel is set to a dimension that corresponds to a selected number of pulses from the carriage pulse generator 134. Similarly, the width of a pixel is set to a dimension that corresponds to the number of pulses from the rotational pulse generator 124. Thus, for ease of explanation, the pixels are shown to be square in FIG. 5*a*; however, it is not required that pixels be square, but only that they be rectangular.

Each column of pixels represents one pass of the workpiece past the focal position of the laser. This column is repeated as many times as is required to reach completely around workpiece 102. A white pixel (not shown in the Figures) represents an off instruction to the laser, that is the laser is emitting no power, and each black pixel represents an on instruction to the laser, that is the laser is emitting a beam. This results in a simple binary file of 1's and 0's where a 1, or white, is an instruction for the laser to shut off and a 0, or black, is an instruction for the laser to turn on.

Referring back to FIG. 4, the contents of an engraving file are sent in a binary form, where 1 is off and 0 is on, by the main computer 142 to the laser 137 via connection 143. By varying the time between each instruction, the duration of the instruction is adjusted to conform to the size of the pixel. After each column of the file is completed, that column is again processed, or repeated, until the entire circumference is completed. While the instructions of a column are being carried out, the traverse drive is moved slightly. The speed of traverse is set so that upon completion of a circumferential engraving, the traverse drive has moved the focusing lens the width of a column of pixels and the next column of pixels is processed. This continues until the end of the file is reached and the file is again repeated in the axial dimension until the total desired width is reached.

In this approach, each pass produces a number of narrow cuts in the material, rather than a large hole. Because these cuts are precisely registered to line up side-by-side and overlap somewhat, the cumulative effect is a hole.

A highly preferred method for making the laser sculpted three dimensional topographical support members is through laser modulation. Laser modulation is carried out by gradually varying the laser power on a pixel by pixel basis. In laser modulation, the simple on or off instructions of raster scan drilling are replaced by instructions that adjust on a gradual scale the laser power for each individual pixel of the laser modulation file. In this manner, a three dimensional structure can be imparted to the workpiece in a single pass over the workpiece.

Laser modulation has several advantages over other methods of producing a three dimensional topographical support member. Laser modulation produces a one-piece, seamless, support member without the pattern mismatches caused by the presence of a seam. With laser modulation, the support member is completed in a single operation instead of multiple operations, thus increasing efficiency and decreasing cost. Laser modulation eliminates problems with the registration of patterns, which can be a problem in a multi-step sequential operation. Laser modulation also allows for the creation of topographical features with complex geometries over a substantial distance. By varying the instructions to the laser, the depth and shape of a feature can be precisely controlled and features that continuously vary in cross section can be formed. Also, with laser sculpting, the regular positions of the apertures relative to one another can be maintained.

Referring again to FIG. 4, during laser modulation, the main computer 142 may send instructions to the laser 137 in other than a simple "on" or "off" format. For example, the simple binary file may be replaced with an 8 bit (byte) format, which allows for a variation in power emitted by the laser of 256 possible levels. Utilizing a byte format, the instruction "11111111" instructs the laser to turn off, "00000000" instructs the laser to emit full power, and an instruction such as "10000000" instructs the laser to emit one-half of the total available laser power.

A laser modulation file can be created in many ways. One such method is to construct the file graphically using a gray scale of a 256 color level computer image. In such a gray scale image, black can represent full power and white can represent no power with the varying levels of gray in between representing intermediate power levels. A number of computer graphics programs can be used to visualize or create such a laser-sculpting file. Utilizing such a file, the power emitted by the laser is modulated on a pixel by pixel basis and can therefore directly sculpts a three dimensional topographical support member. While an 8-bit byte format is described here, other levels, such as 4 bit, 16 bit, 24 bit or other formats can be substituted.

A suitable laser for use in a laser modulation system for laser sculpting is a fast flow $CO_2$ laser with a power output of 2500 watts, although a laser of lower power output could be used. Of primary concern is that the laser must be able to switch power levels as quickly as possible. A preferred switching rate is at least 10 kHz and even more preferred is a rate of 20 kHz. The high power-switching rate is needed to be able to process as many pixels per second as possible.

Figure 5:
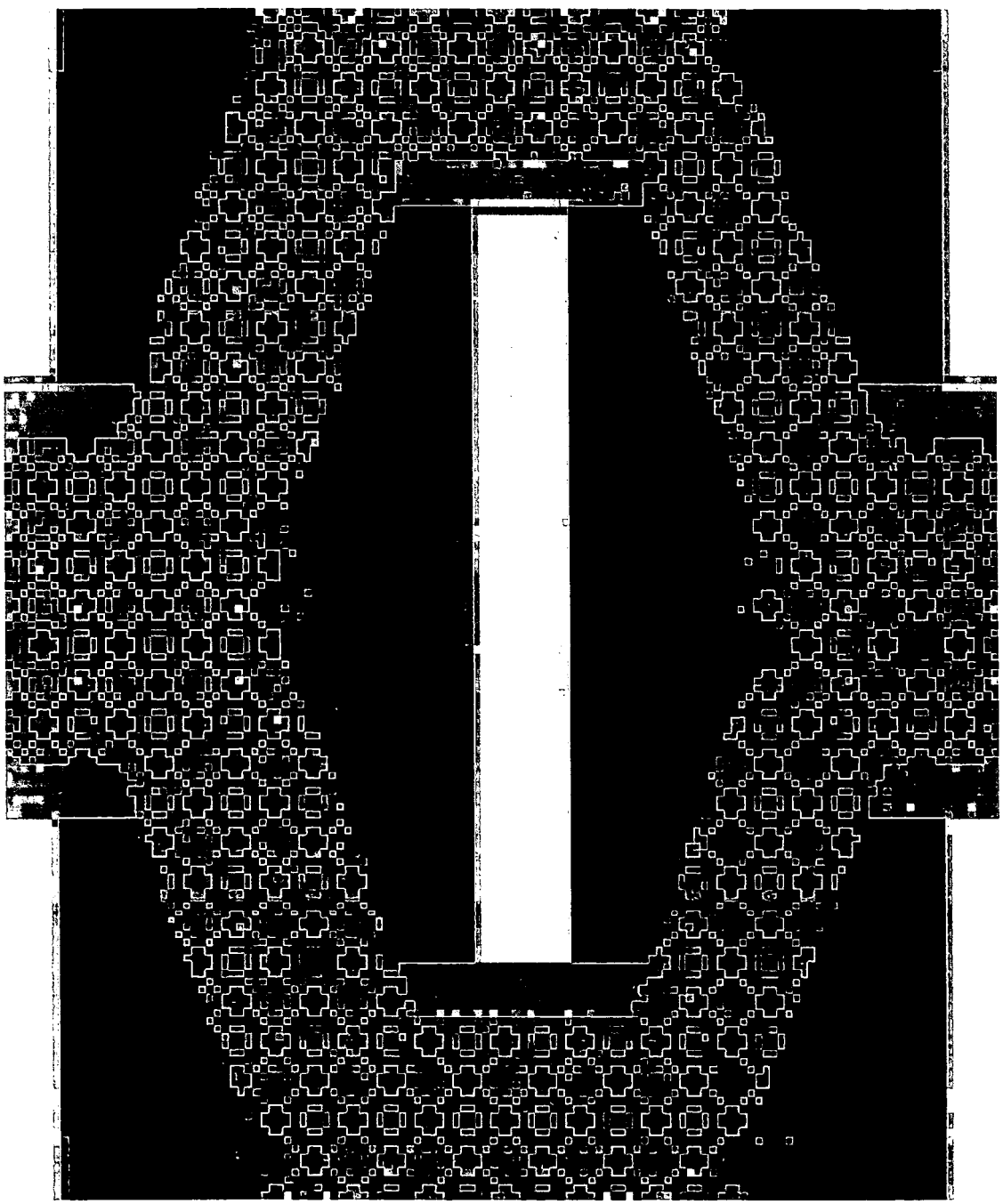
FIG. 5 is a graphical representation of a file to laser sculpt a workpiece to produce a three dimensional topographical support member for producing an apertured film shown in FIGS. 1a-1d.
Figure 5A:
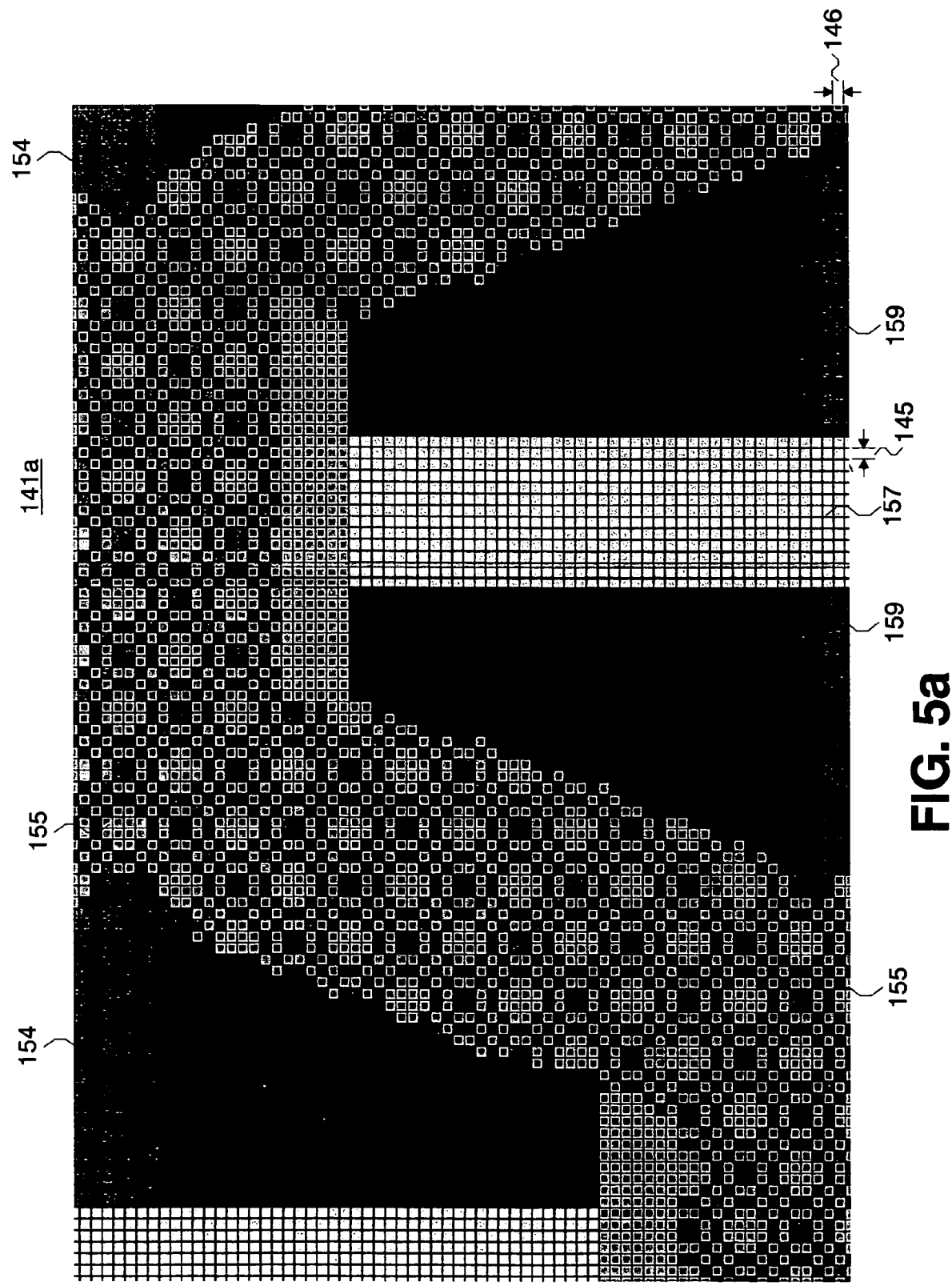
FIG. 5a is a graphical representation of the file shown in FIG. 5 showing an enlarged portion thereof.
Figure 6:
FIG. 6 is a photomicrograph of a workpiece after it was sculpted utilizing the file of FIG. 5.

FIG. 5 is a graphical representation of a laser modulation file, including a repeat element 141*a*, that may be used to form a support member for forming the apertured film shown in FIGS. 1-1*a*. FIG. 5*a* is an enlarged portion of the laser modulation file shown in FIG. 5*b*. In FIGS. 5 and 5*a* the black areas 154*a* indicate pixels where the laser is instructed to emit full power, thereby creating a hole in the support member, which corresponds to apertures 16 in the three-dimensional apertured film 10 illustrated in FIGS. 1*a*-1*d*. The light gray areas 155 in FIGS. 5 and 5*a* indicate pixels where the laser receives instructions to apply a very low level power, thereby leaving the surface of the support member essentially intact. These areas of the support member correspond to the protuberances 11 shown in FIG. 1*a*. The other areas depicted in FIGS. 5 and 5*a*, which are depicted in various levels of gray, represent corresponding levels of laser power and correspond to various features of the film 10 shown in FIGS. 1*a*-1*d*. For example, areas 157 and 159 correspond to cross members 14*a* and 14*b* of the film 10. FIG. 6 is a photomicropgraph of a portion 161 of a support member after it was engraved using the file shown in FIG. 5. The pattern on the portion of support member shown in FIG. 6 is repeated over the surface of the support member to thereby produce the repeating pattern of the film 10 shown in FIGS. 1*a*-1*d*.

Figure 7:
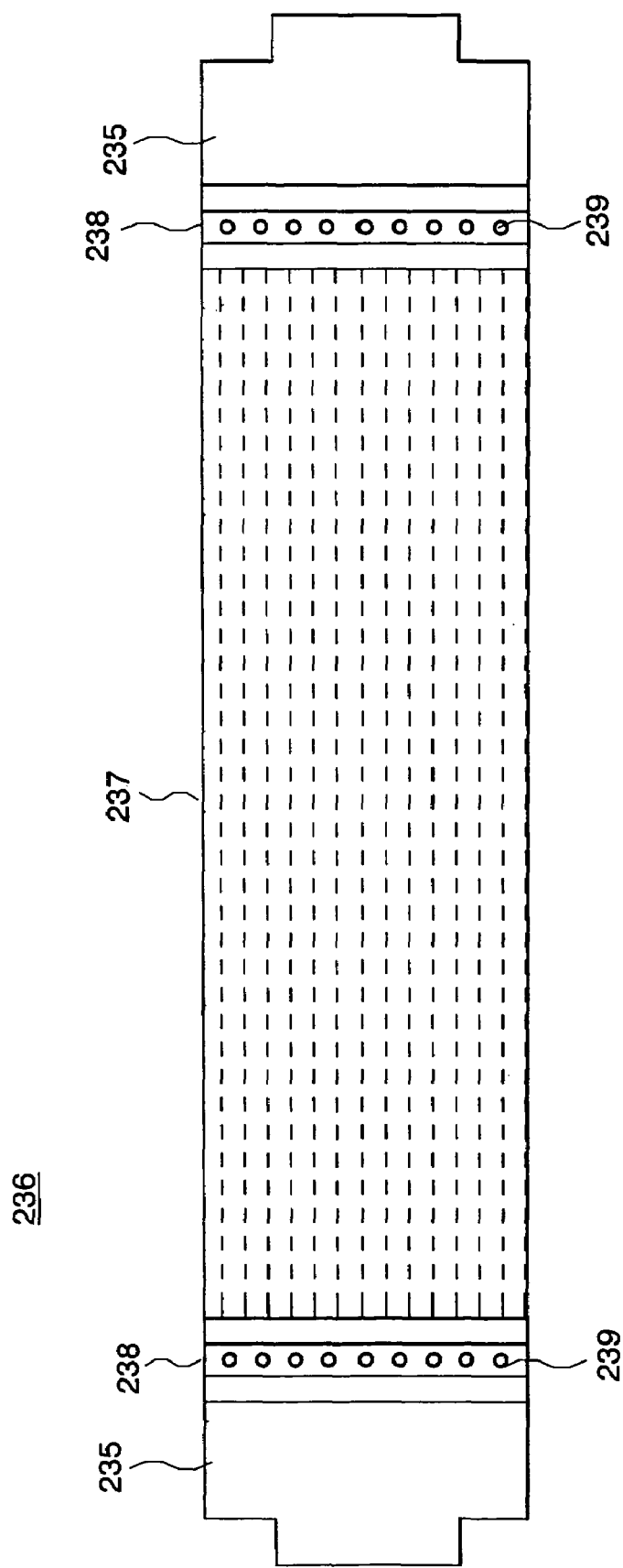
FIG. 7 is a view of a support member used to make a film according to the invention in place on a film-forming apparatus.

Upon completion of the laser sculpting of the workpiece, it can be assembled into the structure shown in FIG. 7 for use as a support member. Two end bells 235 are fitted to the interior of the workpiece 236 with laser sculpted area 237. These end bells can be shrink-fit, press-fit, attached by mechanical means such as straps 238 and screws 239 as shown or by other mechanical means. The end bells provide a method to keep the workpiece circular, to drive the finished assembly, and to fix the completed structure in the aperturing apparatus.

Figure 8:
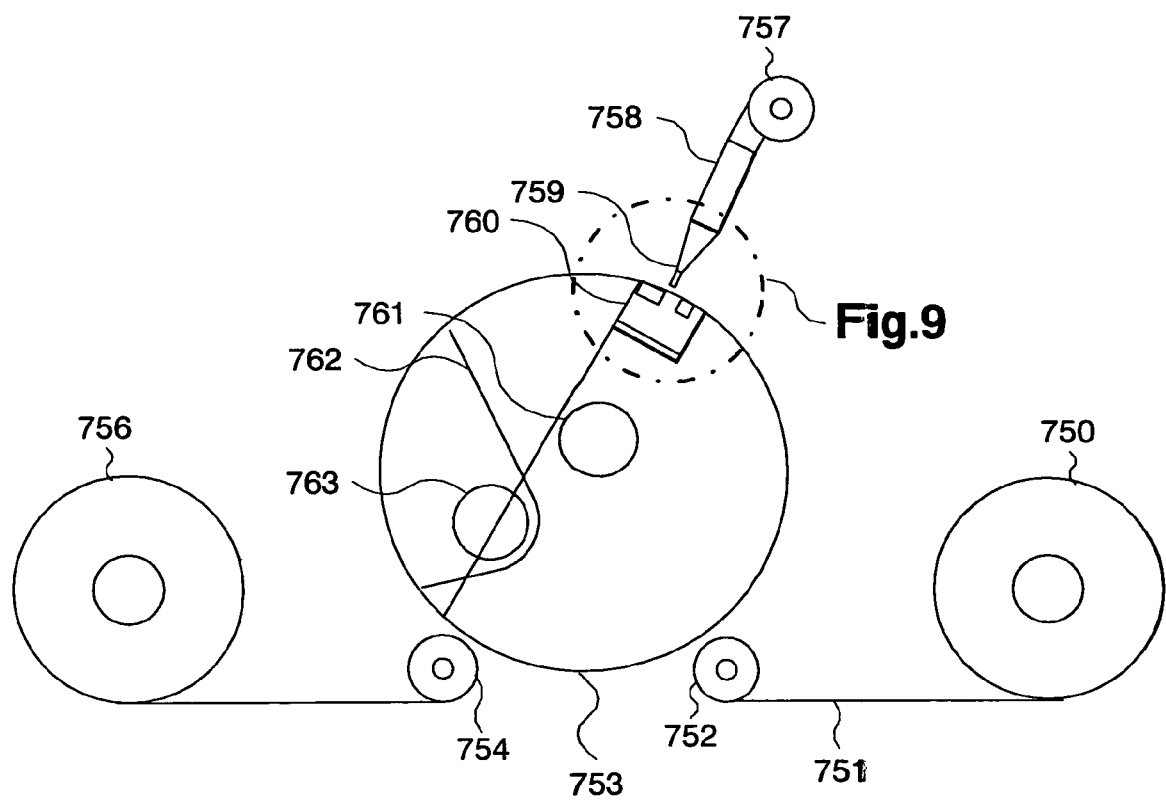
FIG. 8 is a schematic view of an apparatus for producing an apertured film according to the present invention.

A preferred apparatus for producing such three dimensional apertured films is schematically depicted in FIG. 8. As shown here, the support member is a rotatable drum 753. In this particular apparatus, the drum rotates in a counterclockwise direction. Positioned outside drum 753 is a hot air nozzle 759 positioned to provide a curtain of hot air to impinge directly on the film supported by the laser sculpted support member. Means is provided to retract hot air nozzle 759 to avoid excessive heating of the film when it is stopped or moving at slow speed. Blower 757 and heater 758 cooperate to supply hot air to nozzle 759. Positioned inside the drum 753, directly opposite the nozzle 759, is vacuum head 760. Vacuum head 760 is radially adjustable and positioned so as to contact the interior surface of drum 753. A vacuum source 761 is provided to continuously exhaust vacuum head 760.

Cooling zone 762 is provided in the interior of and contacting the inner surface of drum 753. Cooling zone 762 is provided with cooling vacuum source 763. In cooling zone 762, cooling vacuum source 763 draws ambient air through the apertures made in the film to set the pattern created in the aperturing zone. Vacuum source 763 also provides means of holding the film in place in cooling zone 762 in drum 753 and provides means to isolate the film from the effects of tension produced by winding up the film after its aperturing.

Placed on top of laser sculpted support member 753 is a thin, continuous, uninterrupted film 751 of thermoplastic polymeric material.

Figure 9:
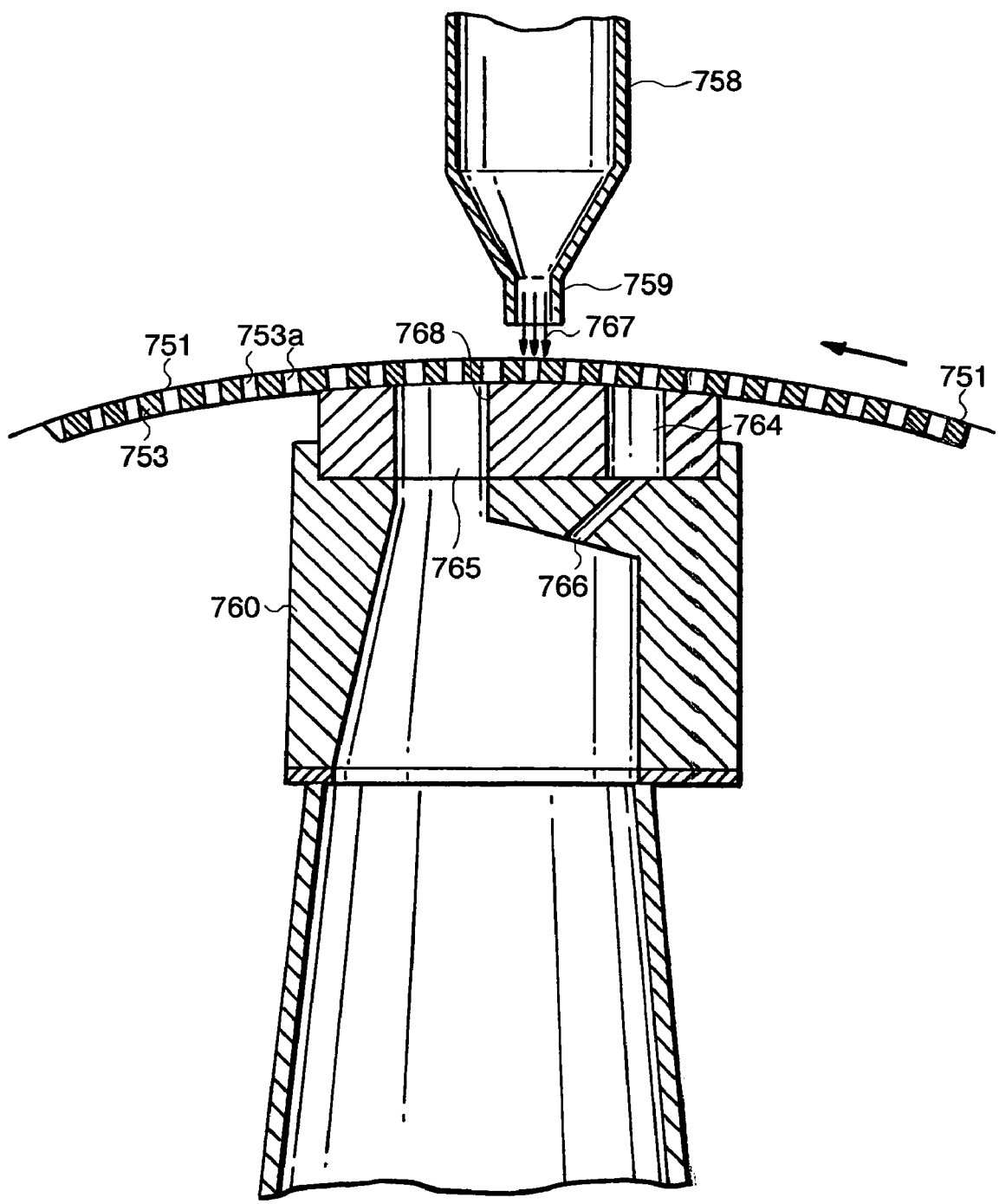
FIG. 9 is a schematic view of the circled portion of FIG. 8.
Figure 10:
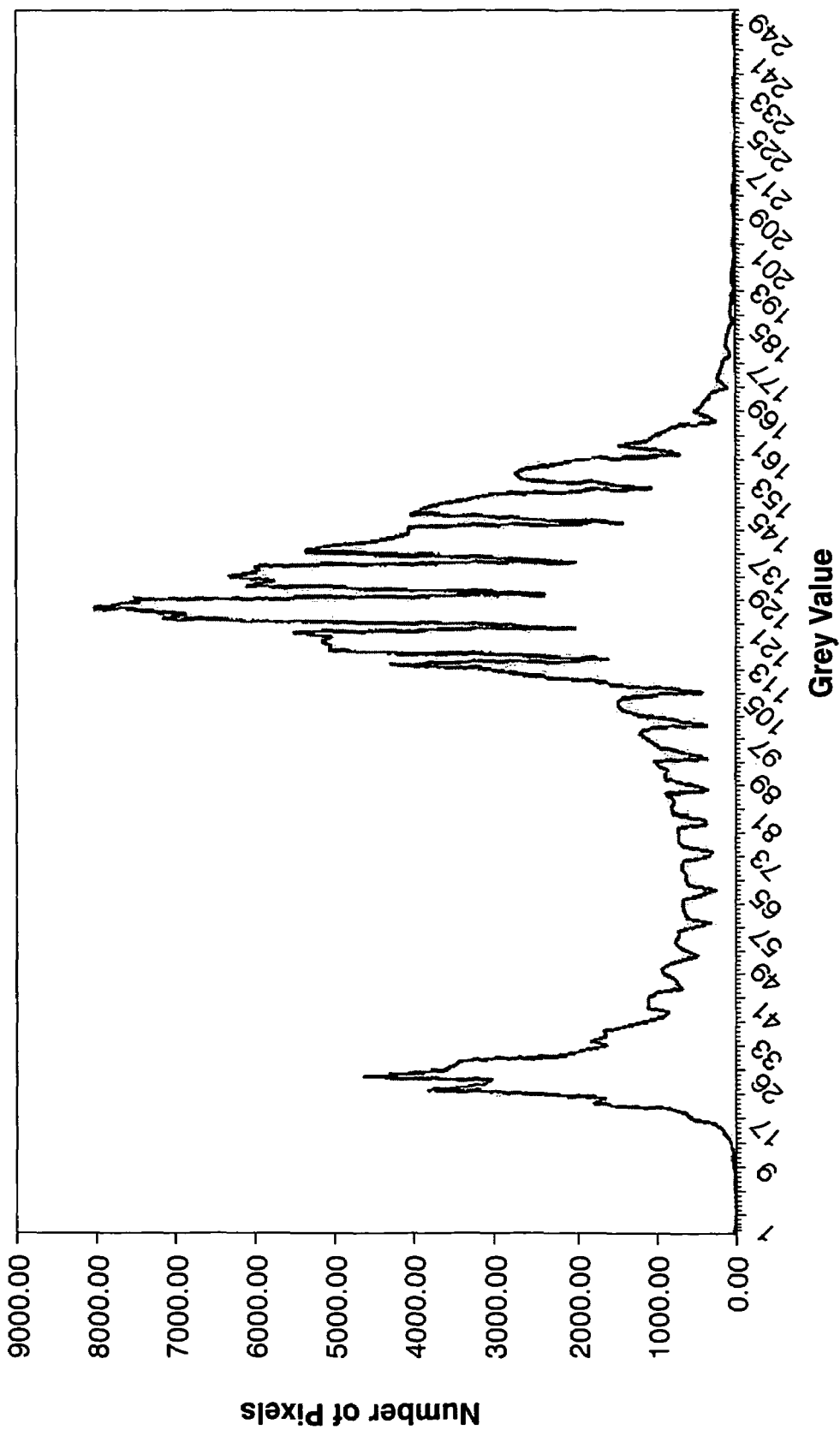
FIG. 10 is an exemplary average histogram representing stain intensity for an absorbent article according to the present invention.

An enlargement of the circled area of FIG. 8 is shown in FIG. 9. As shown in this embodiment, vacuum head 760 has two vacuum slots 764 and 765 extending across the width of the film. However, for some purposes, it may be preferred to use separate vacuum sources for each vacuum slot. As shown in FIG. 23, vacuum slot 764 provides a hold down zone for the starting film as it approaches air knife 758. Vacuum slot 764 is connected to a source of vacuum by a passageway 766. This anchors the incoming film 751 securely to drum 753 and provides isolation from the effects of tension in the incoming film induced by the unwinding of the film. It also flattens film 751 on the outer surface of drum 753. The second vacuum slot 765 defines the vacuum aperturing zone. Immediately between slots 764 and 765 is intermediate support bar 768. Vacuum head 760 is positioned such that the impingement point of hot air curtain 767 is directly above intermediate support bar 768. The hot air is provided at a sufficient temperature, a sufficient angle of incidence to the film, and at a sufficient distance from the film to cause the film to become softened and deformable by a force applied thereto. The geometry of the apparatus ensures that the film 751, when softened by hot air curtain 767, is isolated from tension effects by hold-down slot 764 and cooling zone 762 (FIG. 22). Vacuum aperturing zone 765 is immediately adjacent hot air curtain 767, which minimizes the time that the film is hot and prevents excessive heat transfer to support member 753.

Referring to FIGS. 8 and 9, a thin flexible film 751 is fed from a supply roll 750 over idler roll 752. Roll 752 may be attached to a load cell or other mechanism to control the feed tension of the incoming film 751. The film 751 is then placed in intimate contact with the support member 753. The film and support member then pass to vacuum zone 764. In vacuum zone 764, the differential pressure further forces the film into intimate contact with support member 753. The vacuum pressure then isolates the film from the supply tension. The film and support member combination then passes under hot air curtain 767. The hot air curtain heats the film and support member combination, thus softening the film.

The heat-softened film and the support member combination then pass into vacuum zone 765 where the heated film is deformed by the differential pressure and assumes the topography of the support member. The heated film areas that are located over open areas in the support member are further deformed into the open areas of the support member. If the heat and deformation force are sufficient, the film over the open areas of the support member is ruptured to create apertures.

The still-hot apertured film and support member combination then passes to cooling zone 762. In the cooling zone, a sufficient quantity of ambient air is pulled through the now-apertured film to cool both the film and the support member.

The cooled film is then removed from the support member around idler roll 754. Idler roll 754 may be attached to a load cell or other mechanism to control winding tension. The apertured film then passes to finish roll 756, where it is wound up.

Absorbent System—First Absorbent Layer

U.S. Pat. No. 6,515495 discuses the absorbent system employed in the absorbent article according to the present invention, the subject matter of which is hereby incorporated by reference.

Adjacent to the cover layer 842 on its inner side and bonded to the cover layer 842 is a first absorbent layer 846 that forms part of the absorbent system 848. The first absorbent layer 846 provides the means of receiving body fluid from the cover layer 842 and holding it until an underlying second absorbent layer has an opportunity to absorb the fluid and therefore acts as a fluid transfer or acquisition layer.

The first absorbent layer 846 is, preferably, more dense than and has a larger proportion of smaller pores than the cover layer 842. These attributes allow the first absorbent layer 846 to contain body fluid and hold it away from the outer side of the cover layer 842, thereby preventing the fluid from rewetting the cover layer 842 and its surface. However, the first absorbent layer 846 is, preferably, not so dense as to prevent the passage of the fluid through the layer 846 into the underlying second absorbent layer 848.

The first absorbent layer 846 may be composed of fibrous materials such as wood pulp, polyester, rayon, flexible foam, or the like, or combinations thereof. The first absorbent layer 846 may also comprise thermoplastic fibers for the purpose of stabilizing the layer and maintaining its structural integrity. The first absorbent layer 846 may be treated with surfactant on one or both sides in order to increase its wettability, although generally the first absorbent layer 846 is relatively hydrophilic and may not require treatment. The first absorbent layer 846 is preferably bonded or adhered on both sides to the adjacent layers, i.e., the cover layer 842 and an underlying second absorbent layer 848.

Materials particularly suitable for use in the first absorbent layer 846, which the inventors have found contribute to reducing the rewet potential, have a density in the range of about 0.04 to 0.05 g/cc, a basis weight in the range from about 80 to 110 g/m$^2$, a thickness in the range of about 2 to 3 mm and in particular a thickness of 2.6 mm. Examples of suitable materials for the first absorbent layer are through air bonded pulp sold by Buckeye of Memphis, Tenn., under the designation VIZORB 3008, which has a basis weight of 110 g/m$^2$ and VIZORB 3010, which has a basis weight of 90 g/m$^2$.

Absorbent System—Second Absorbent Layer

Immediately adjacent to and bonded to the first absorbent layer 846 is the second absorbent layer 848.

In one embodiment, the second absorbent layer 848 is a blend or mixture of cellulosic fibers and superabsorbent disposed in and amongst fibers of that pulp. In a specific example, the second absorbent layer 848 is a material containing from about 40 weight percent to about 95 weight percent cellulosic fibers and from about 5 weight percent to about 60 weight percent SAP (superabsorbent polymers). The material has a water content of less than about 10 weight percent. As used herein, the phrase "weight percent" means weight of substance per weight of final material. By way of example, 10 weight percent SAP means 10 g/m² SAP per 100 g/m² basis weight of the material.

Cellulosic fibers that can be used in the second absorbent layer 848 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

The second absorbent layer 848 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA60N Type II*, and the product offered by Chemical International, Inc. of Palatine, Ill., under the designation of 2100A*.

In a specific example, the second absorbent layer 848 is a material containing from about 40 to about 95 weight percent cellulosic fibers and, more specifically, from about 60 to about 80 weight percent cellulosic fibers. Such a material may contain from about 5 to about 60 weight percent SAP, preferably from about 20 to about 55 weight percent SAP, even more preferably from about 30 to about 45 weight percent SAP, and most preferably about 40 weight percent SAP.

In a preferred embodiment, the second absorbent layer 848 is manufactured by using air-laying means. The second absorbent layer 848 of the present invention is of high density and in a specific example has a density of greater than about 0.25 g/cc. Specifically, the second absorbent layer 848 may have a density in the range of from about 0.30 g/cc to about 0.50 g/cc. More specifically, the density is from about 0.30 g/cc to about 0.45 g/cc and, even more specifically, from about 0.30 g/cc to about 0.40 g/cc.

Air-laid absorbents are typically produced with a low density. To achieve higher density levels, such as the examples of the second absorbent layer 848 given above, the air-laid material is compacted using calendars. Compaction is accomplished using means well known in the art. Typically such compaction is carried out at a temperature of about 100 degrees C. and a load of about 130 Newtons per millimeter. The upper compaction roll is typically made of steel while the lower compaction roll is a flexroll having a hardness of about 85 SH D. It is preferred that both the upper and lower compaction rolls be smooth, although the upper roll can be engraved.

The second absorbent layer 848 can be prepared over a wide range of basis weights. The second absorbent layer 848 can have a basis weight in the range of from about 100 g/m² to about 700 g/m². In a specific example, the basis weight ranges from about 150 g/m² to about 400 g/m².

Preferably, the basis weight ranges from about 200 g/m² to about 350 g/m² and, more preferably, to about 300 g/m². The second absorbent layer 848 functions synergistically with the first absorbent layer to reduce the rewet potential. The first absorbent layer, having a relatively open pore structure, readily absorbs and disperses liquid laterally within its bulk and readily transfers the liquid to the receiving surface of the second absorbent layer. In turn, the second absorbent layer, having good capillarity efficiently draws liquid into its bulk from the first absorbent layer. Once the liquid has been absorbed into superabsorbent polymer, the liquid cannot be subsequently released by applying pressure. Therefore, the liquid absorbed into the superabsorbent material becomes permanently entrapped. At the same time, the strength with which the second absorbent layer intakes liquid from the first absorbent layer helps to reduce the proportion of liquid held in the first absorbent layer, thereby reducing the amount of liquid that returns to the cover layer when the napkin is subjected to mechanical loading. Furthermore, the first absorbent layer has a relatively high capillarity so that any concentration of liquid in the first absorbent layer resulting from mechanical loading can be redistributed within the material to lower concentrations, again reducing the amount of liquid which can return to the cover layer.

In a specific embodiment, the second absorbent layer contains in the range from about 30 to 40 weight percent superabsorbent material, has a basis weight in the range from about 200 to 400 g/m² and a density in the range from about 0.2 to 0.45 g/cc.

Figure 13A:
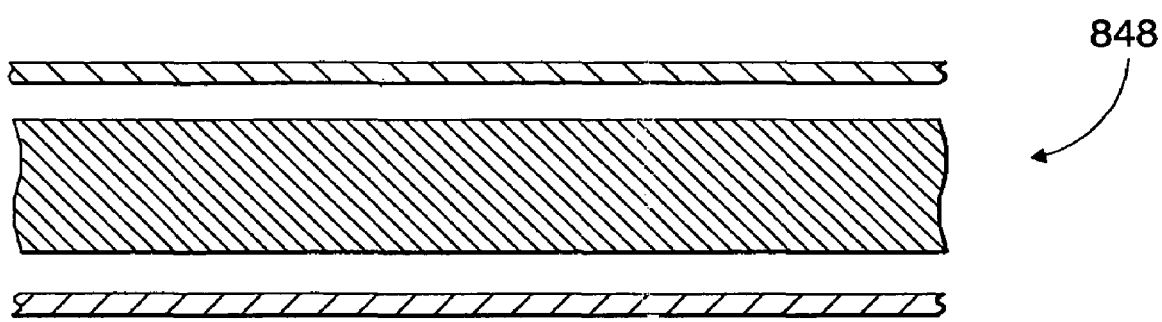
FIGS. 13a and 13b shows three and four layer embodiments of a second absorbent layer that can be used in the sanitary napkin of an embodiment of the invention.
Figure 13B:
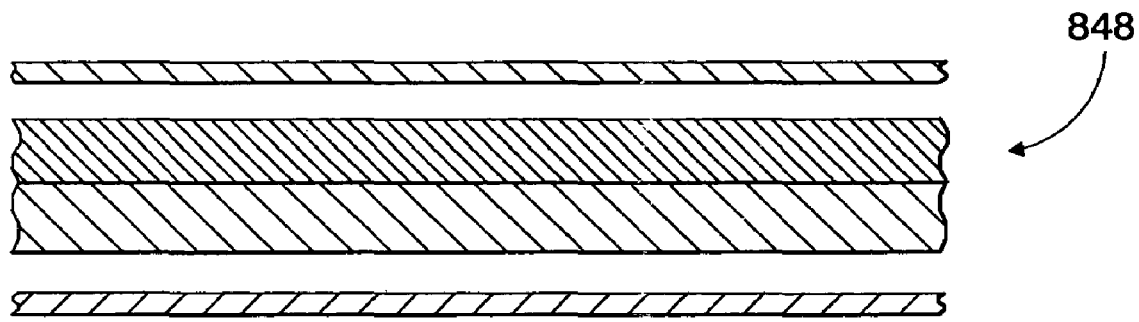

As shown in FIG. 13a and FIG. 13b, the second absorbent layer 848 can be formed as three or four lamina or strata. Those strata include a bottom layer, one or two middle layers and a top layer. Specific examples of three and four layer material are set forth below. The SAP can be included in any or all of the layers. The concentration (weight percent) of SAP in each layer can vary as can the nature of the particular SAP.

An interesting characteristic of the second absorbent layer 848 is its ability to retain SAP when subjected to mechanical stress. The second absorbent layer 848 retained over 85 percent by weight of its SAP content when subjected to 10 minutes of rigorous shaking. Specifically, a material of this invention retains over 90 percent, more specifically over 95 percent and, even more specifically over 99 percent of its SAP under these mechanical stresses. The percent of SAP retained was determined by shaking the material in a Ro-Tap Sieve Shaker manufactured by W. S. Tyler Co., Cleveland Ohio. More specifically, the sample is placed in a 28-mesh (Tyler series) sieve. Additional sieves of 35-mesh and 150-mesh were attached to the first sieve forming a column of increasingly fine sieves. The column of sieves was capped on either end to prevent the loss of fiber and/or SAP. The sieve column was placed in the shaker and agitated for 10 minutes. The amount of SAP granules shaken loose from the sample, "free SAP", was determined by combining the residue contained in each of the sieves and separating the cellulosic fiber from the SAP.

Even where prepared as from multiple layers, the final thickness of the formed second absorbent layer 848 is low. The thickness can vary from about 0.5 mm to about 2.5 mm. In a specific example, the thickness is from about 1.0 mm to about 2.0 mm and, even more specifically, from about 1.25 mm to about 1.75 mm.

One embodiment of the second absorbent layer 848 particularly well suited for use in the sanitary napkin 800 is depicted in FIG. 13. Such second absorbent layer 848 has a basis weight of from about 200 g/m² to about 350 g/m² and a density between about 0.3 g/cc and 0.5 g/cc. In a specific example, the density is from about 0.3 g/cc to about 0.45 g/cc and, more specifically about 0.4 g/cc.

The second absorbent layer 848 depicted in FIG. 13 is air-laid as three strata: a bottom layer of pulp (without superabsorbent) with a basis weight of about 25 g/m$^2$; a middle layer with a basis weight of about 150 g/m$^2$ and which contains from about 10 to about 30 g/m$^2$ superabsorbent and from about 120 g/m$^2$ to about 140 g/m$^2$ pulp; and a top layer of pulp (without superabsorbent) with a basis weight of about 25 g/m$^2$. Relative to the total basis weight of the second absorbent layer 848, the level of superabsorbent ranges from about 5 to about 15 weight percent (g/m$^2$ of superabsorbent per g/m$^2$ material). In a specific example, the level of superabsorbent is from about 7.5 weight percent to about 12.5 weight percent of the material. More specifically, the material contains about 10 weight percent of superabsorbent. Thus, the middle layer of the material could contain from about 15 g/m$^2$ to about 25 g/m$^2$ superabsorbent and from about 125 g/m$^2$ to about 135 g/m$^2$ pulp and, more specifically about 20 g/m$^2$ superabsorbent and about 130 g/m$^2$ pulp. The middle layer containing pulp and superabsorbent can be laid down as a homogeneous blend or as a heterogeneous blend wherein the level of superabsorbent varies with proximity to the bottom layer.

In another embodiment, the second absorbent layer 848 is air-laid as four strata. In this embodiment, the middle layer referred to above is replaced with two middle layers; a first middle layer adjacent the top layer and a second middle layer adjacent the bottom layer. Each of the first and second middle layers independently comprises from about 10 to about 30 g/m.sup.2 superabsorbent and from about 40 g/m$^2$ to about 65 g/m$^2$ pulp. When it is desired to keep absorbed fluid away from the cover layer 842, the amount of superabsorbent in the first and second middle layers is adjusted such that there is a higher level of superabsorbent in the second middle layer. The superabsorbent in the first and second middle layers can be the same or a different superabsorbent.

In one embodiment, the cellulosic fiber for use in the second absorbent layer 848 is wood pulp. There are certain characteristics of wood pulp that make it particularly suitable for use. Cellulose in most wood pulps has a crystalline form known as Cellulose I which can be converted to a form known as Cellulose II. In the second absorbent layer 848, wood pulp with a substantial portion of the cellulose as Cellulose II could be used. Similarly, pulps having an increased fiber curl value are advantageous. Finally, pulps having reduced levels of hemicellulose are preferred. Means for treating pulps so as to optimize these characteristics are well known in the art. By way of example, treating wood pulp with liquid ammonia is known to convert cellulose to the Cellulose II structure and to increase the fiber curl value. Flash drying is known to increase the fiber curl value of pulp. Cold caustic treatment of pulp decreases hemicellulose content, increases fiber curl and converts cellulose to the Cellulose II form. Thus, it could be advantageous that the cellulosic fibers used to produce the material of this invention contain at least a portion of cold caustic treated pulp.

A description of the cold caustic extraction process can be found in U.S. patent application Ser. No. 08/370,571, filed on Jan. 18, 1995, pending which application is a continuation-in-part application of U.S. patent application Ser. No. 08/184,377, now abandoned filed on Jan. 21, 1994. The disclosures of both of these applications are incorporated in their entirety herein by reference.

Briefly, a caustic treatment is typically carried out at a temperature less than about 60 degree C., but preferably at a temperature less than 50 degree C., and more preferably at a temperature between about 10 degree C. to 40 degree C. A preferred alkali metal salt solution is a sodium hydroxide solution newly made up or as a solution by-product in a pulp or paper mill operation, e.g., hemicaustic white liquor, oxidized white liquor and the like. Other alkali metal salts such as ammonium hydroxide and potassium hydroxide and the like can be employed. However, from a cost standpoint, the preferable salt is sodium hydroxide. The concentration of alkali metal salts is typically in a range from about 2 to about 25 weight percent of the solution, and preferably from about 6 to about 18 weight percent. Pulps for high rate, fast absorbing applications are preferably treated with alkali metal salt concentrations from about 10 to about 18 weight percent.

For further details on the structure and the method of construction of the second absorbent layer 848, the reader is invited to refer to the U.S. Pat. No. 5,866,242 granted on Feb. 2, 1999 to Tan et al. The contents of this document are hereby incorporated by reference.

Barrier Layer

Underlying the absorbent system 848 is a barrier layer 850 comprising liquid-impervious material so as to prevent liquid that is entrapped in the absorbent system 848 from egressing the sanitary napkin and staining the wearer's undergarment. The barrier layer 50 is preferably made of polymeric film, although it may be made of liquid-impervious air-permeable material such as repellent-treated, non-woven or microporous films or foams.

The cover layer 842 and the barrier layer 850 are joined along their marginal portions so as to form an enclosure or flange seal that maintains the absorbent system 848 captive. The joint may be made by means of adhesives, heat-bonding, ultrasonic bonding, radio frequency sealing, mechanical crimping, and the like and combinations thereof.

Procedure for Measuring the Thickness of a Sanitary Article

As indicated earlier, the sanitary napkin 800 has a thickness of about 5 mm or less. The apparatus required to measure the thickness of the sanitary napkin is a footed dial (thickness) gauge with stand, available from Ames, with a 2" diameter foot at a pressure of 0.07 psig and a readout accurate to 0.001". A digital type apparatus is preferred. If the sanitary napkin sample is individually folded and wrapped, the sample is unwrapped and carefully flattened by hand. The release paper is removed from the sample and it is repositioned back gently across the positioning adhesive lines so as not to compress the sample, ensuring that the release paper lies flat across the sample. Flaps (if any) are not considered when taking the thickness reading in the center of the sample.

The foot of the gauge is raised and the sample is placed on the anvil such that the foot of the gauge is approximately centered the sample (or in the location of interest on the sample of interest). When lowering the foot, care must be taken to prevent the foot dropping onto the sample or undue force being applied. A load of 0.07 p.s.i.g. is applied to the sample and the read out is allowed to stabilize for approximately 5 seconds. The thickness reading is then taken. The thickness of the release paper covering the positioning adhesive is deducted from the total thickness.

Fluid Handling and Stain Masking Test Method

The sanitary napkin according to the present invention has improved fluid handling and stain masking characteristics. The fluid handling and fluid masking test method set forth below consists of three constituent tests including: (1) fluid penetration test; (2) rewet test and (3) masking value test. The same five test samples should be used when conducting all three tests. That is, a clean sample should not be used for each test but rather the same sample should be tested for fluid penetration and then rewet and then masking value.

The test fluid used for the fluid penetration test, rewet test and masking value according to the test procedures set forth below may be any synthetic menstrual fluid having the following properties: (1) a viscosity of approximately 30 centipoise; and (2) Hunter color values as follows: L=about 17, a=about 7, b=about 1.5. The L Hunter values of the test fluid were measured by placing a quantity of the test fluid in a glass dish to a depth of 0.25".

Procedure for Fluid Penetration Time

Fluid Penetration Time is measured by placing a sample to be tested under a Fluid Penetration Test orifice plate. The orifice plate consists of a 7.6 cm×25.4 cm plate of 1.3 cm thick polycarbonate with an elliptical orifice in its center. The elliptical orifice measures 3.8 cm along its major axis and 1.9 cm along its minor axis. The orifice plate is centered on the sample to be tested. A graduated 10 cc syringe containing 7 ml of test fluid is held over the orifice plate such that the exit of the syringe is approximately 3 inches above the orifice. The syringe is held horizontally, parallel to the surface of the test plate. The fluid is then expelled from the syringe at a rate that allows the fluid to flow in a stream vertical to the test plate into the orifice and a stop watch is started when the fluid first touches the sample to be tested. The stop watch is stopped when surface of the sample first becomes visible within the orifice. The elapsed time on the stop watch is the Fluid Penetration Time. The average Fluid Penetration Time (FPT) is calculated from the results of testing five samples.

Procedure for Measuring Rewet Potential

The rewet potential is a measure of the ability of a napkin or other article to hold liquid within its structure when the napkin contains a relatively large quantity of liquid and is subjected to external mechanical pressure. The rewet potential is determined and defined by the following procedure.

The apparatus required for the test includes a stop watch with an accuracy to 1 sec and at least 5 minutes duration, a graduated glass cylinder of 10 ml capacity and having an internal diameter of approximately 12 mm, a quantity of test fluid, and a fluid penetration test orifice plate. The test plate is rectangular and made from Lexan and is 25.4 cm (10.0 inches) long by 7.6 cm (3.0 inches) wide by 1.27 cm (0.5 inches) thick. A concentric, elliptical orifice is formed through the plate having a major axis of length 3.8 cm and being parallel to the length of the plate and a minor axis of width 1.9 cm and being parallel to the width of the plate.

The apparatus further includes a weighing machine or balance capable of weighing to an accuracy of .+-.0.001 g, a quantity of NuGauze general use sponges (10 cm.times. 10 cm) (4 inches.times.4 inches)—4 ply from Johnson & Johnson Medical Inc. Product Code 3634 (available from Johnson & Johnson Hospital Services, re: order number 7634), a standard weight of 2.22 kg (4.8 pounds) having dimensions 5.1 cm (2 inches) by 10.2 cm (4.0 inches) by approximately 5.4 cm (2.13 inches) which applies a pressure of 4.14 kPa (0.6 psi) over the 5.1 by 10.2 cm (2 inches by 4 inches) surface.

For purposes of the test procedure set forth herein, the same five samples used for the fluid penetration test should be used for the rewet potential test. That is, after the fluid penetration test has been conducted in the manner set forth above, the same five samples should be immediately tested for rewet potential.

If the napkin is folded, the creases are removed as far as possible by flattening and if the napkin is curved, the side gathers are cut through several times so that the sample can be flattened.

Two sponges are folded with the creased edges placed opposing each other to create a layered structure of approximately 5 cm by 10 cm by 16 plies. A 16 ply sponge for each napkin sample to be tested is then weighed to the nearest 0.001 grams. The preconditioned sanitary napkin or other article is placed on a level surface, without removing the release paper and with the cover layer facing upwards.

After the test fluid is applied within the orifice plate in the FPT test described above and as soon as the cover layer of the napkin first appears through the top surface of the fluid, the stop watch is started and an interval of 5 minutes is measured. After 5 minutes have elapsed, the orifice plate is removed and the napkin is positioned on a hard level surface with the cover layer facing upwards. One pre-weighed 16 ply layered sponge is placed on and centered over the wetted area and the standard 2.22 kg weight is placed on top of the 16 ply layered sponge. Immediately after placing the sponge and weight on the napkin, the stop watch is started and after a 3 minute interval has elapsed, the standard weight and 16 ply layered sponge are quickly removed. The wet weight of the 16 ply layered sponge is measured and recorded to the nearest 0.001 grams. The rewet value is then calculated as the difference in grams between the weight of the wet 16 ply layered sponge and the dry 16 ply layered sponge.

The above measurement is repeated for the five samples and, if necessary, the weight is wiped clean before each run. The average rewet potential is obtained by averaging the value obtained from the five samples.

When conducting the above method, it is important that the tests are performed at a temperature of 21.+-0.1.degree. C. and 65.+-0.2% relative humidity.

Masking Value Test

The following test measures an absorbent articles ability to hide a fluid stain, e.g., menstrual fluid.

After each of the five samples are subjected to the penetration test and the rewet test as described above, they are immediately imaged, after fluid testing, at 50× using a Scalar USB Microscope model UM02-SUZ-01, utilizing the included light source. The Scalar scope was set at hue saturation and intensity with auto-exposure enabled. Five random areas were imaged from each sample, and the images saved as 640×480 pixel 24 bit true-color image files in the "bmp" format. Thus, a total of 25 images (5 images/assembly for each of 5 assemblies) were obtained.

The original "bmp" images were then opened in Image Pro Plus ver 4.0 software, a product of Media Cybermetics, LP. The images were then converted, in Image Pro Plus, from their original 24 bit true-color format into an 8-bit gray scale image. Image Pro Plus's histogram function was then applied to the images and a histogram of the images gray values was then constructed. This provides a count of the number of pixels at a particular gray value which gray value ranges from "0" black to "255" white. The data from the histogram was then transferred into a Microsoft Excel 2000 worksheet, utilizing DDE (Windows dynamic data exchange).

The DDE to Excel 2000 then produces a worksheet that contains 25 columns, each containing 256 rows. Each of the columns in the worksheet contains the histogram values for a single image. Each column consists of 256 values, which is a count of the number of pixels in the image, which have a corresponding value from 0 to 255. Each of the rows was then averaged to create an average histogram for that particular material.

A typical average histogram shows a bi-modal distribution of the gray area, representing the stained area of the test assembly, and the white area, representing the unstained area of the test assembly. Examination of the average histograms demonstrated a plateau between the gray region and the white region, and that all of the stained area was defined by a gray value of 90 or less. Thus the stain area of a material can be determined by the sum of gray values between 0 and 90, with lower values representing lower gray areas and thus better masking. The summation of the gray values of 90 or less is the "Masking Value".

When tested according to the above procedures, the sanitary napkins according to the present invention preferably have a masking value of less than about 115,000, an average fluid penetration time of less than about 45 seconds and an average rewet of less than about 0.05 grams. Preferably, the sanitary napkins according to the present invention have a masking value of less than about 100,000, more preferably less than about 90,000 and most preferably less than about 85,000. Preferably, the sanitary napkins according to the present invention have an average fluid penetration time of less than 40 seconds and most preferably less than 35 seconds.

The sanitary napkin according to the present invention provides surprisingly good masking characteristics for a given average fluid penetration time and average rewet potential.

Although specific embodiments of the invention have been described above, it is intended that the present application cover the modifications and variations of the invention provided that they come with the scope of the appended claims and their equivalents.

I claim:

1. A sanitary napkin comprising:
   an apertured film body-facing cover layer having an open area between about 20% and about 30%,
   an absorbent system adjacent said cover layer for receiving liquid therefrom,
   a fluid impermeable garment facing layer,
   said napkin having a masking value of less than about 115,000, an average fluid penetration time of less than about 45 seconds and an average rewet of less than about 0.05 grams according to the test procedure described herein;
   wherein said absorbent system includes a blend of cellulosic fibers and superabsorbent material;
   wherein said absorbent system comprises a first absorbent layer and a second absorbent layer, said second absorbent layer having a basis weight of from about 100 g/m$^2$ to about 700 g/m$^2$ which has been air-laid as a bottom layer of pulp, a middle layer of pulp intermixed with superabsorbent polymer, and a top layer containing at least some pulp; and
   wherein the middle layer comprises a first middle layer adjacent the bottom layer and a second middle layer adjacent the top layer.

2. The sanitary napkin according to claim 1, wherein said masking value is less than about 100,000.

3. The sanitary napkin according to claim 2, wherein said masking value is less than about 90,000.

4. The sanitary napkin according to claim 3, wherein said masking value is less than about 85,000.

5. The sanitary napkin according to claim 1, wherein said average fluid penetration time is less than 40 seconds.

6. The sanitary napkin according to claim 5, wherein said average fluid penetration time is less than 35 seconds.

7. The sanitary napkin according to claim 1, wherein said absorbent system includes a superabsorbent material.

8. The sanitary napkin according to claim 1, wherein said second absorbent layer has a density of more than about 0.25 g/cc.

9. The sanitary napkin according to claim 8, wherein said second absorbent layer has a density in the range from about 0.3 g/cc to about 0.5 g/cc.

10. The sanitary napkin according to claim 9, wherein said second absorbent layer has a density in the range from about 0.3 g/cc to about 0.45 g/cc.

11. The sanitary napkin according to claim 1, wherein said second absorbent layer includes from about 20 weight percent to about 55 weight percent suberabsorbent polymer.

12. The sanitary napkin according to claim 11, wherein said second absorbent layer includes from about 30 weight percent to about 45 weight percent superabsorbent polymer.

13. The sanitary napkin according to claim 12, wherein said second absorbent layer includes about 40 weight percent superabsorbent polymer.

14. The sanitary napkin according to claim 1, wherein said second absorbent layer has a basis weight in the range from about 150 g/m$^2$ to about 350 g/m$^2$.

15. The sanitary napkin according to claim 14, wherein said second absorbent layer has a basis weight in the range from about 200 g/m$^2$ to about 300 g/m$^2$.

16. The sanitary napkin according to claim 15, wherein said second absorbent layer has a basis weight of about 250 g/m$^2$.

17. The sanitary napkin according to claim 1, wherein said first absorbent layer is air laid over said second absorbent layer.

18. The sanitary napkin according to claim 17, wherein said first absorbent layer comprises thermoplastic fibers.

19. The sanitary napkin according to claim 17, wherein said first absorbent layer comprises a material having a density in the range from about 0.04 to 0.05 g/cc.

20. The sanitary napkin according to claim 17, wherein said first absorbent layer comprises a material having a basis weight in the range from about 80 g/m$^2$ to about 110 g/m$^2$.

21. The sanitary napkin according to claim 1, wherein said first absorbent layer has a thickness in the range from about 2 mm to about 3 mm.

22. The sanitary napkin according to claim 1, wherein said second absorbent layer includes from about 5 weight percent to about 60 weight percent superabsorbent polymer.

23. The sanitary napkin according to claim 1, wherein the thickness of the sanitary napkin is less than about 3 mm.

24. The sanitary napkin according to claim 23, wherein the thickness of the sanitary napkin is about 2.8 mm.

* * * * *